(12) United States Patent
Yoshinaka et al.

(10) Patent No.: US 9,044,038 B2
(45) Date of Patent: Jun. 2, 2015

(54) METHOD OF IMPROVING SWEETNESS QUALITIES OF STEVIA EXTRACT

(75) Inventors: Koji Yoshinaka, Toyonaka (JP); Masanori Mie, Toyonaka (JP); Maki Yamamoto, Toyonaka (JP); Hiroshige Ueno, Toyonaka (JP); Tetsuya Tokumura, Toyonaka (JP); Takeshi Aya, Toyonaka (JP)

(73) Assignee: SAN-EI GEN F.F.I., INC., Toyonaka-Shi, Osaka (JP)

( * ) Notice: Subject to any disclaimer, the term of this patent is extended or adjusted under 35 U.S.C. 154(b) by 267 days.

(21) Appl. No.: 12/742,152

(22) PCT Filed: Nov. 12, 2008

(86) PCT No.: PCT/JP2008/070617
§ 371 (c)(1),
(2), (4) Date: Jun. 28, 2010

(87) PCT Pub. No.: WO2009/063921
PCT Pub. Date: May 22, 2009

(65) Prior Publication Data
US 2010/0267847 A1    Oct. 21, 2010

(30) Foreign Application Priority Data

Nov. 12, 2007 (JP) ................... 2007-293524
Mar. 21, 2008 (JP) ................... 2008-073694
May 15, 2008 (JP) ................... 2008-128637

(51) Int. Cl.
| | |
|---|---|
| A61K 9/00 | (2006.01) |
| A23G 3/36 | (2006.01) |
| A23F 5/24 | (2006.01) |
| A23L 1/06 | (2006.01) |
| A23L 1/068 | (2006.01) |
| A23L 1/22 | (2006.01) |
| A23L 1/236 | (2006.01) |
| A23L 1/238 | (2006.01) |
| A23L 2/06 | (2006.01) |
| A23L 2/60 | (2006.01) |
| A61K 36/00 | (2006.01) |
| A61K 36/28 | (2006.01) |
| A61K 36/42 | (2006.01) |

(52) U.S. Cl.
CPC . *A23G 3/36* (2013.01); *A23F 5/243* (2013.01); *A23L 1/06* (2013.01); *A23L 1/068* (2013.01); *A23L 1/22091* (2013.01); *A23L 1/2366* (2013.01); *A23L 1/238* (2013.01); *A23L 2/06* (2013.01); *A23L 2/60* (2013.01); *A23V 2002/00* (2013.01); *A61K 36/00* (2013.01); *A61K 36/28* (2013.01); *A61K 36/42* (2013.01)

(58) Field of Classification Search
USPC ....................................................... 424/400
See application file for complete search history.

(56) References Cited

U.S. PATENT DOCUMENTS

| | | | |
|---|---|---|---|
| 6,432,464 B1* | 8/2002 | Andersen et al. ............. | 426/548 |
| 2007/0009638 A1 | 1/2007 | Takemori et al. | |
| 2007/0082106 A1 | 4/2007 | Lee et al. | |
| 2007/0134390 A1 | 6/2007 | Prakash et al. | |
| 2007/0178193 A1 | 8/2007 | Chang et al. | |
| 2009/0148568 A1 | 6/2009 | Kawamura et al. ............. | 426/89 |
| 2011/0052755 A1* | 3/2011 | Fiorenza et al. ................. | 426/3 |

FOREIGN PATENT DOCUMENTS

| | | |
|---|---|---|
| CN | 1795744 A | 7/2006 |
| JP | 52-90667 A | 7/1977 |
| JP | 53-104771 A | 9/1978 |
| JP | 58-116674 | 7/1983 |
| JP | 61-212257 A | 9/1986 |
| JP | 2-276553 A | 11/1990 |
| JP | 08-013251 | 2/1996 |
| JP | 10-234331 A | 9/1998 |
| JP | 11-46701 A | 2/1999 |
| JP | 2000-166506 A | 6/2000 |
| JP | 2000-287642 | 10/2000 |
| JP | 2001-95502 A | 4/2001 |
| JP | 2001-211854 A1 | 8/2001 |
| JP | 2001-231485 | 8/2001 |
| JP | 2002-223721 A | 8/2002 |
| JP | 2003-180288 A | 7/2003 |
| JP | 2003-274911 A | 9/2003 |
| JP | 2006-81544 A | 3/2006 |
| JP | 2006-238828 A1 | 9/2006 |
| JP | 2006-340650 A | 12/2006 |
| WO | 2006/072921 A2 | 7/2006 |
| WO | WO 2008/112991 A2 | 9/2008 |
| WO | WO 2009/016374 A1 | 2/2009 |

OTHER PUBLICATIONS

King and Kinghorn (Arch Pharm Res vol. 25, No. 6, 725-746, 2002).*

(Continued)

*Primary Examiner* — David J Blanchard
*Assistant Examiner* — Devang Thakor
(74) *Attorney, Agent, or Firm* — Kratz, Quintos & Hanson, LLP

(57) ABSTRACT

The present invention provides a technique for improving the sweetness of stevia extract. A composition having an excellent sweetness quality can be obtained by combining rebaudioside A, which is a main sweetness component of stevia extract, with mogroside V, which is a main sweetness component of siraitia grosvenorii extract, at a weight ratio of 95:5 to 60:40. By using the mixture described above as a sweetener, favorable sweetness can be imparted to various products, such as foods, medicines or quasi drugs.

1 Claim, No Drawings

(56) References Cited

OTHER PUBLICATIONS

Delloyd's Lab Tech, downloaded Nov. 1, 2012.*
"Saishin Koryo no Jiten" (New Encyclopedia of Flavors), Asakura Publishing Co., Ltd., May 10, 2000, 1st edition, pp. 535-537 (specification p. 5.).
Supplementary European Search Report dated Mar. 14, 2012, in counterpart European Application No. EP 08850549.
Dietary Supplements, Courtesy Letters (Letters of Objection), LET 604 HFS-810 to Sweet Aloha Farms, May 6, 2002, pp. 1-5.
S.S. Schiffman, et al.; "Investigation of Synergism in Binary Mixtures of Sweeteners"; *Brain Research Bulletin*; vol. 38; No. 2; Jan. 1, 1995; pp. 105-120.
Walter H. Glinsmann, et al.; "GRAS Exemption Claim for the Use of Luo Han Fruit Concentrate as a Flavor Modifier and Sweetener in Conventional Foods"; *GRAS Notice 000301*; Jul. 22, 2009; pp. 1-113.
International Search Report for International Application No. PCT/JP2008/070617 dated Feb. 24, 2009.

\* cited by examiner

METHOD OF IMPROVING SWEETNESS QUALITIES OF STEVIA EXTRACT

TECHNICAL FIELD

The present invention relates to a method for improving the sweetness of stevia extract.

More specifically, a first aspect of the present invention relates to a technology for improving the sweetness quality of rebaudioside A, which is a main sweetness component of stevia extract (e.g., a sweetener or orally administered composition comprising rebaudioside A, and a method for applying sweetness to an orally administered composition).

A second aspect of the present invention relates to a technology for improving the sweetness quality of stevia extract itself (e.g., a sweetness quality improving method, a sweetness quality improving agent, and a sweetener or orally administered composition in which the sweetness quality has been improved by the above sweetness quality improving method).

A third aspect of the present invention relates to a technology for accelerating the sweetness expression of stevia extract in the oral cavity (e.g., a method for accelerating sweetness expression, and a sweetener or orally administered composition in which the sweetness expression has been accelerated by the above method).

BACKGROUND ART

Hitherto, high-intensity sweeteners have been widely used to impart sweetness to foods, beverages, medicines and quasi drugs, as well as to adjust the taste thereof. In particular, due to the recent rise in health concerns, non- or low-calorie high-intensity sweeteners, and high-intensity sweeteners with low caries-producing effects are widely utilized.

Examples of high-intensity sweeteners include synthetic sweeteners such as aspartame, sucralose, neotame, acesulfame potassium, and the like; and natural sweeteners such as stevia extract, siraitia grosvenori extract, thaumatin, and the like. Of these, natural sweeteners such as stevia extract have become favored as a result of the recent trend toward natural products.

Natural sweeteners, however, exhibit a sweetness quality different from that of sucrose, exhibit a rough taste in their sweetness, and leaves a lingering sweetness (a remaining aftertaste) in the mouth. In addition to the above, stevia extract, in particular, has drawbacks such as a characteristic bitterness and a lack of sweetness due to its slow sweetness expression in the oral cavity.

The term "sweetness quality" used herein refers to the quality of the sweetness itself. In view of an overall evaluation of sweetness, considering its richness, body, fullness, and low distinctiveness, a quality that is closer to that of sucrose is regarded as being better quality. The term "rough taste" used herein refers to a bitter, astringent, sour, stimulating taste, and the like, other than sweetness.

A number of proposals have been made to overcome the above drawbacks inherent in high-intensity sweeteners such as stevia extract.

For example, it has been proposed to use, as an agent for improving the taste of a high-intensity sweetener, nigerooligosaccharide (Patent Document 1), cellooligosaccharide (Patent Document 2), a solvent extract of roasted coffee (Patent Document 3), and the like. Further, as a taste improving agent, which improves the long-lasting aftertaste of aspartame, the use of sodium chloride (Patent Document 4), the combined use of potassium aluminum sulfate and naringin (Patent Document 5), and the like, have been proposed.

Methods involving the use of a sweet flavor (a sucrose flavor) such as maltol to improve the sweetness quality of a high-intensity sweetener have also been proposed. Sucrose flavors are prepared by using an aromatic component having a granulated-sugar-like aroma, such as maltol, ethyl maltol or the like, as a main component, together with a minor constituent such as sucrose lactone, cyclotene, or the like, which is associated with brown sugar and maple syrup; and a natural starting material such as molasses extract, honey extract, and the like (Non-Patent Document 1).

For example, Patent Document 6 suggests using a sweet flavor such as maltol or furaneol, in addition to a high-intensity sweetener such as acesulfame potassium or sucralose, in order to improve the watery taste of sugarless candies that are composed mainly of sugar alcohol. Patent Document 7 teaches a feed additive for livestock comprising a mixture of a stevia extract and a flavoring agent containing a sweet flavor such as maltol or furaneol. Patent Document 7 further teaches that the addition of the feed additive to feed for livestock, including cattle and swine, can make the feed more palatable, and mitigate diarrhea in livestock. None of the above documents, however, discloses or suggests a method for accelerating the sweetness expression of stevia extract. These documents even fail to disclose that stevia extract suffers from slow sweetness expression.

Patent Document 8 teaches that a sweet flavor such as maltol is effective for improving the sweetness quality of aspartame (by expressing fullness and body. However, Patent Document 8 discloses in Example 1 that the sweet flavor is effective only for aspartame, and has no effect on other high-intensity sweeteners such as stevia extract, acesulfame potassium, and the like.

Methods for improving the sweetness quality of a high-intensity sweetener that involve the combined use of several sweeteners have also been proposed. Patent Document 9, for example, discloses using at least one sweetener selected from siraitia grosvenorii extract, stevia extract, licorice extract, and amacha extract, in combination with a syrup containing erythritol and siraitia grosvenorii glycoside in order to improve its sweetness quality. Patent Document 10 teaches that the further addition of stevia and citric acid to guava tea extract and siraitia grosvenorii extract can be used to prepare a healthy tea having a refreshing sweetness and sweet-sour taste. However, Patent Documents 9 and 10 only disclose using siraitia grosvenorii extract (or siraitia grosvenorii glycoside) in an amount equal to or more than the amount of stevia extract, and neither of these documents discloses or suggests using rebaudioside A, which is a main sweetness component of stevia extract, and mogroside V, which is a main sweetness component of siraitia grosvenorii extract, at a specific weight ratio, in order to improve the sweetness quality.

Thaumatin itself can be used as a sweetener. However, because thaumatin exhibits a flavor-enhancing effect and a bitterness-masking effect, it is regarded as a high-intensity sweetener that can also be used as a flavor enhancer, for example. As a method for improving taste quality using thaumatin, Patent Document 11 discloses a method for preparing a dressing, etc., having natural sweetness and good flavor, by using, in addition to thaumatin, at least one member selected from stevia extract, licorice extract, siraitia grosvenorii extract, amacha extract, and the like. Patent Document 12 teaches a method for producing a sweetness composition comprising thaumatin together with at least one member selected from licorice extract, stevia extract, and siraitia grosvenorii extract. However, Patent Documents 11 and 12 nowhere mention combining thaumatin with rebaudioside A, which is a main sweetness component of stevia extract, and mogroside V, which is a main sweetness component of siraitia grosvenorii extract.

Patent Document 1: Japanese Unexamined Patent Publication No. H10-234331

Patent Document 2: Japanese Unexamined Patent Publication No. 2002-223721

Patent Document 3: Japanese Unexamined Patent Publication No. 2006-81544

Patent Document 4: Japanese Unexamined Patent Publication No. S61-212257

Patent Document 5: Japanese Unexamined Patent Publication No. S52-90667

Patent Document 6: Japanese Unexamined Patent Publication No. 2006-340650

Patent Document 7: Japanese Unexamined Patent Publication No. 2001-95502

Patent Document 8: Japanese Unexamined Patent Publication No. H2-276553

Patent Document 9: Japanese Unexamined Patent Publication No. H11-46701

Patent Document 10: Japanese Unexamined Patent Publication No. 2003-274911

Patent Document 11: Japanese. Unexamined Patent Publication No. 2000-166506

Patent Document 12: Japanese Unexamined Patent Publication Application No. S53-104771

Non-Patent Document 1: Saishin Koryo no Jiten (New Encyclopedia of Flavors) (Asakura Publishing Co., Ltd.), pp. 535-537, May 10, 2000, first edition

DISCLOSURE OF THE INVENTION

Problems to be Solved by the Invention

As mentioned above, many attempts have been made to improve the sweetness quality of high-intensity sweeteners in order to obtain a high-intensity sweetener having a sweetness quality as close as possible to that of sucrose. However, none of these attempts were sufficient as a method for overcoming stevia extract drawback, in particular, a rough taste in sweetness (bitterness), a long-lasting sweetness in the mouth (a remaining aftertaste), and a lack of sweetness due to slow sweetness expression in the oral cavity.

In view of the above, the present invention aims to provide a method for improving the sweetness quality of stevia extract or rebaudioside A, which is a main sweetness component thereof.

More specifically, a first object of the present invention is to provide a method for improving the sweetness quality of rebaudioside A, which is a main sweetness component of stevia extract, and to provide orally administered compositions, such as sweeteners, foods, and beverages, in which the sweetness quality has been improved by the method.

A second object of the present invention is to provide a method for improving the sweetness quality of stevia extract itself; a sweetness quality improving agent that is useful in the method; and orally administered compositions, such as sweeteners, foods, beverages, and the like, in which the sweetness quality has been improved by the sweetness quality improving method.

A third object of the present invention is to provide a method for accelerating the sweetness expression of stevia extract in the oral cavity; and compositions, such as sweeteners, foods and beverages, in which the sweetness expression in the oral cavity has been accelerated by this method.

Means for Solving the Problems

The present inventors conducted extensive research to achieve the first object, and found the following. That is, by adjusting the compounding ratio of rebaudioside A, which is a main sweetness component of stevia extract, to mogroside V, which is a main sweetness component of siraitia grosvenorii extract, to a range of 95:5 to 60:40 (weight ratio), in particular, from 94:6 to 75:25 (weight ratio), the aforesaid drawbacks of stevia extract regarding sweetness quality can be eliminated, making the production of a composition having an excellent sweetness quality possible. In addition, the use of the mixture as a sweetener enables excellent sweetness to be applied to various products such as foods, medicines and quasi drugs, which are orally administered or used for the oral cavity.

The present inventors further conducted extensive research to achieve the second object, and found the following. That is, the addition of at least one member selected from the group consisting of gentiooligosaccharides, naringins, highly branched cyclic dextrins, magnesium chloride and magnesium sulfate, to stevia extract can eliminate the drawbacks of the sweetness quality of stevia extract; in particular, a lingering sweetness in the mouth (a remaining aftertaste) can be improved.

The present inventors yet further conducted extensive research to achieve the third object, and found the following. That is, the addition of a sweet flavor such as maltol or the like to stevia extract at a weight ratio of 200:1 to 6,000:1, preferably 300:1 to 6,000:1, can eliminate the sweetness quality drawbacks of stevia extract, in particular, the slow sweetness expression in the oral cavity; with the accelerated sweetness expression of stevia extract, a lack of sweetness and lingering sweetness (a remaining aftertaste) can be improved.

The present invention was accomplished based on the above findings, and encompasses the following aspects.
(I) Improvement in Sweetness Quality of Rebaudioside A
(I-1) Sweetener Comprising Rebaudioside A
 (I-1-1) A sweetener comprising rebaudioside A and mogroside V at a weight ratio of 95:5 to 60:40 (rebaudioside A:mogroside V).
 (I-1-2) The sweetener according to (I-1-1), which further comprises 0.01 to 3 parts by mass of thaumatin per total 100 parts by mass of rebaudioside A and mogroside V.
(I-2) Composition Orally Administered or Used for the Oral Cavity
 (I-2-1) A composition orally administered or used for an oral cavity having sweetness and containing rebaudioside A and mogroside V at a weight ratio of 95:5 to 60:40 (rebaudioside A:mogroside V).
 (I-2-2) The composition according to (I-2-1), which comprises rebaudioside A and mogroside V in a total amount of 10 ppm to 5,000 ppm.
 (I-2-3) The composition according to (I-2-1) or (I-2-2), which further comprises 0:01 to 3 parts by mass of thaumatin per total 100 parts by mass of rebaudioside A and mogroside V.
(I-3) Application of Sweetness to Compositions Orally Administered or Used for the Oral Cavity
 (I-3-1) A method for applying sweetness to a composition orally administered or used for an oral cavity comprising the step of: adding rebaudioside A and mogroside V to a composition orally administered or used for the oral cavity so that the weight ratio of rebaudioside A to mogroside V becomes 95:5 to 60:40.

(I-3-2) The method according to (I-3-1), wherein rebaudioside A and mogroside V are added to the composition orally administered or used for the oral cavity so that the total content of rebaudioside A and mogroside V becomes 10 ppm to 5,000 ppm.

(I-3-3) The method according to (I-3-1) or (I-3-2), wherein thaumatin is added to the composition orally administered or used for the oral cavity so that the content of the thaumatin becomes 0.01 to 3 parts by mass per total 100 parts by mass of rebaudioside A and mogroside V.

(I-3-4) The method according to any one of (I-3-1) to (I-3-3), wherein the composition orally administered or used for the oral cavity is a food or beverage, or a medicine or quasi drug that is orally administered or used for the oral cavity.

(II) Improvement in Sweetness Quality of Stevia Extract (II-1) Agent for Improving Taste of Stevia Extract (II-1-1) A sweetness quality improving agent comprising at least one active ingredient selected from the group consisting of gentiooligosaccharides, naringins, highly branched cyclic dextrins, magnesium chloride and magnesium sulfate.

(II-2) Method for Improving Sweetness of Stevia Extract (II-2-1) A method for improving sweetness quality of a stevia extract comprising the step of: adding a sweetness quality improving agent containing at least one active ingredient selected from the group consisting of gentiooligosaccharides, naringins, highly branched cyclic dextrins, magnesium chloride and magnesium sulfate to a stevia extract.

(II-2-2) The method for improving the sweetness quality according to (II-2-1), comprising the step of: adding a sweetness quality improving agent of (II-1-1) to stevia extract or a stevia extract-containing composition that is orally administered or used for an oral cavity.

(II-2-3) The method for improving the sweetness quality according to (II-2-2), wherein the sweetness quality improving agent is used so that the content of each of the active ingredients per part by mass of the stevia extract falls within the following ranges:

Gentiooligosaccharide: 5 to 100 parts by mass, and preferably 5 to 50 parts by mass;

Naringin: 0.01 to 1 part by mass, and preferably 0.01 to 0.5 part by mass;

Highly branched cyclic dextrin: 0.1 to 50 parts by mass, and preferably 0.5 to 30 parts by mass;

Magnesium chloride: 0.05 to 5 parts by mass, and preferably 0.05 to 3 parts by mass; and Magnesium sulfate: 0.05 to 5 parts by mass, and preferably 0.05 to 3 parts by mass.

(II-2-4) The method according to (II-2-2) or (II-2-3), wherein the composition orally administered or used for the oral cavity is a food or beverage, or a medicine or quasi drug that is orally administered or used for the oral cavity.

(II-3) Stevia Extract-Containing Sweetener (II-3-1) A sweetener comprising a stevia extract and at least one member selected from the group consisting of gentiooligosaccharides, naringins, highly branched cyclic dextrins, magnesium chloride and magnesium sulfate.

(II-3-2) The sweetener according to (II-3-1), which comprises the following ranges of at least one member selected from the group consisting of gentiooligosaccharides, naringins, highly branched cyclic dextrins, magnesium chloride and magnesium sulfate, per part by mass of stevia extract:

Gentiooligosaccharide: 5 to 100 parts by mass, and preferably 5 to 50 parts by mass;

Naringin: 0.01 to 1 part by mass, and preferably 0.01 to 0.5 part by mass;

Highly branched cyclic dextrin: 0.1 to 50 parts by mass, and preferably 0.5 to 30 parts by mass;

Magnesium chloride: 0.05 to 5 parts by mass, and preferably 0.05 to 3 parts by mass; and Magnesium sulfate: 0.05 to 5 parts by mass, and preferably 0.05 to 3 parts by mass.

(II-4) Composition Orally Administered or Used for the Oral Cavity (II-4-1) A composition orally administered or used for the oral cavity having sweetness and containing stevia extract and at least one member selected from the group consisting of gentiooligosaccharides, naringins, highly branched cyclic dextrins, magnesium chloride and magnesium sulfate.

(II-4-2) The composition according to (II-4-1), which comprises the following ranges of at least one member selected from the group consisting of gentiooligosacchardes, naringins, highly branched cyclic dextrins, magnesium chloride and magnesium sulfate per part by mass of stevia extract contained in the composition orally administered or used for the oral cavity:

Gentiooligosaccharide: 5 to 100 parts by mass, and preferably 5 to 50 parts by mass;

Naringin: 0.01 to 1 part by mass, and preferably 0.01 to 0.5 part by mass;

Highly branched cyclic dextrin: 0.1 to 50 parts by mass, and preferably 0.5 to 30 parts by mass;

Magnesium chloride: 0.05 to 5 parts by mass, and preferably 0.05 to 3 parts by mass, and Magnesium sulfate: 0.05 to 5 parts by mass, and preferably 0.05 to 3 parts by mass.

(III) Acceleration of Sweetness Expression of Stevia Extract (III-1) Method for Accelerating Sweetness Expression of Stevia Extract in an Oral Cavity (III-1-1) A method for accelerating sweetness expression of a stevia extract in an oral cavity comprising the step of: combining 200 to 6,000 parts by mass of stevia extract per part by mass of sweet flavor.

(III-1-2) The method according to (III-1-1), wherein the sweet flavor is at least one member selected from the group consisting of maltol, ethyl maltol, sotolon, cyclotene, furaneol, and homofuraneol.

(III-1-3) The method according to (III-1-1), wherein the sweet flavor is maltol.

(III-2) Sweetener (III-2-1) A sweetener comprising 200 to 6,000 parts by mass of stevia extract per part by mass of sweet flavor.

(III-2-2) The sweetener according to (III-2-1), wherein the sweet flavor is at least one member selected from the group consisting of maltol, ethyl maltol, sotolon, cyclotene, furaneol, and homofuraneol.

(III-2-3) The sweetener according to (III-2-1), wherein the sweet flavor is maltol.

(III-3) Composition Orally Administered or Used for the Oral Cavity (III-3-1) A composition that is orally administered or used for an oral cavity having sweetness and comprising 200 to 6,000 parts by mass of stevia extract per part by mass of sweet flavor.

(III-3-2) The composition according to (III-3-1), wherein the sweet flavor is at least one member selected from the group consisting of maltol, ethyl maltol, sotolon, cyclotene, furaneol, and homofuraneol.

(III-3-3) The composition according to (III-3-1), wherein the sweet flavor is maltol.

(III-3-4) The composition according to any one of (III-3-1) to (III-3-3), which comprises 10 ppm to 5,000 ppm of stevia extract.

Effect of the Invention

The sweetener comprising rebaudioside A, which is the first aspect of the present invention, has an excellent sweetness quality that is similar to sucrose. This sweetener can apply excellent sweetness to various compositions. Further, the additional use of thaumatin together with rebaudioside A and mogroside V can produce a sweetener having an excellent and more sucrose-like sweetness quality.

The second aspect of the present invention can provide a novel usage of gentiooligosaccharides, naringins, highly branched cyclic dextrins, magnesium chloride and magnesium sulfate, i.e., a usage as a sweetness quality improving agent of stevia extract. According to this aspect, the use of the above sweetness quality improving agent can improve the sweetness quality of stevia extract; in particular, lingering sweetness (a remaining aftertaste) can be improved. The present invention can thereby provide a sweetener having an excellent sweetness quality by improving the known drawbacks of stevia extract (e.g. bitterness, remaining aftertaste, and slow sweetness expression).

The third aspect of the present invention can improve the known drawbacks of stevia extract, such as the slow rate of sweetness expression in the oral cavity, and accelerate the sweetness expression, thereby eliminating the drawbacks, such as a lack of sweetness, and lingering sweetness (a remaining aftertaste).

BEST MODE FOR CARRYING OUT THE INVENTION (I) Improvement in Sweetness Quality of Rebaudioside A
(I-1) Sweetener One of the features of the sweetener of the present invention is that it comprises rebaudioside A and mogroside V at a weight ratio of 95:5 to 60:40.

Rebaudioside A is a known steviol glycoside, which is a main sweetness component contained in stevia extract. Rebaudioside A has a degree of sweetness (sweetness intensity) 150 to 450 times that of sucrose. The rebaudioside A targeted by the present invention includes enzyme-treated rebaudioside A obtained by transferring glucose, fructose or like saccharide to rebaudioside A using α-glucosyltransferase or the like.

The rebaudioside A used in the present invention may be, but is not limited to, purified rebaudioside A, and may be a mixture with other steviol glycosides (such as stevioside, rebaudioside B, rebaudioside C, rebaudioside D, rebaudioside, dulcoside A, rubusoside, and steviolbioside). When a mixture is used, the content of rebaudioside A is preferably 70% by mass or more per the total amount of the mixture. This is because the greater the content of steviol glycosides such as stevioside other than rebaudioside A becomes, the less the effects on the present invention, in particular, the improvement in sweetness quality due to thaumatin tend to become.

The rebaudioside A used in the present invention may be prepared by subjecting leaves or stems at *Stevia Rebaudiana Bertoni* in the composite family to extraction and purification. However, commercially available products may also be conveniently used. Examples of such commercially available products include Rebaudio J-100 (produced by Morita Kagaku Kogyo Co., Ltd.), Chrysanta 99-P (produced by Dainippon Ink and Chemicals, Incorporated), etc. These products contain 80% by mass or more of rebaudioside A.

Mogroside V is a known triterpene-based glucoside, which is a main sweetness component contained in siraitia grosvenorii extract. Mogroside V has a degree of sweetness about 300 times that of sucrose.

Similar to rebaudioside A, mogroside V may be, but is not limited to, a purified product and may be a mixture with other triterpene-based glucosides (such as mogrol, mogroside $IE_1$, mogroside $IA_1$, mogroside IIE, mogroside III, mogroside IVa, mogroside IVE, siamenoside, 11-oxo-mogroside, and 5α, 6α-epoxymogroside). When a mixture is used, the content of mogroside V is preferably 5% or more per the total amount of the mixture.

The mogroside V used in the present invention may be prepared by subjecting the fruits of siraitia grosvenori in the gourd family to extraction and purification. However, commercially available products may also be conveniently used. One example of such commercially available products is LUO HAN GUO CONCENTRATE EXTRACT POWDER (Siraitia Grosvenori Extract Powder: produced by San-Ei Gen F.F.I., Inc.). The product contains 5% by mass of mogroside V.

As described above, the sweetener of the present invention contains rebaudioside A and mogroside V in a weight ratio of 95:5 to 60:40. The proportion of rebaudioside A to mogroside V is preferably 94:6 to 75:25, and more preferably 90:10 to 75:25 (weight ratio). When the content of mogroside V exceeds 40 parts by mass per 60 parts by mass of rebaudioside A, the sweetness quality cannot be improved. When the content of mogroside V exceeds 50 parts by mass per 50 parts by mass of rebaudioside A, i.e., the content of mogroside V exceeds that of rebaudioside A in a sweetener, the sweetness quality tends to be inferior to that of a sweetener in which rebaudioside A is used singly.

The sweetener of the present invention may contain thaumatin in addition to rebaudioside A and mogroside V. By using thaumatin in combination with mogroside V, the sweetness quality of rebaudioside A can be further improved, and a sweetness quality similar to that of sucrose can be attained.

Thaumatin is obtained from the seeds of *Thaumatococcus daniellii* BENTH, which is a perennial plant in the Marantaceae family. Thaumatin a sweet component having a molecular weight of about 21,000 and containing protein as its main component. Thaumatin has a very high sweetness intensity, i.e., 3,000 to 8,000 times that of sucrose.

The content of thaumatin is generally 0.01 to 3 parts by mass, preferably 0.05 to 2 parts by mass, and more preferably 0.1 to 1 part by mass per total 100 parts by mass of rebaudioside A and mogroside V contained in the sweetener.

The thaumatin can be prepared by subjecting the aril of *Thaumatococcus daniellii* fruit to water extraction and purification. However, commercially available products may also be conveniently used. One example of such commercially available products is SAN SWEET T (produced by San-Ei Gen F.F.I., Inc.). SAN SWEET T consists of 100% by mass of thaumatin.

There is no limitation to the form of the sweetener of the present invention, and the sweetener may take any form including a powder, a granule, a tablet, a capsule and like solid states; or a syrup, an emulsion, a liquid, a gel and like semi-solid or liquid states.

The sweetener of the present invention can be prepared by mixing rebaudioside A and mogroside V, and optionally with thaumatin, at the ratio described above. Depending on the form, pharmacologically acceptable carriers or carriers that may be added to foods and beverages may also be added during the preparation. Examples of such carriers include lactose, glucose, fructose, sucrose, high-fructose corn syrup and like saccharides; sorbitol, erythritol, lactitol, maltitol, mannitol, xylitol, isomalt and like sugar alcohols; isomalto-oligosaccharide, galacto-oligosaccharide, fructo-oligosaccharide and like oligosaccharides; dextrin, cellulose, gum arabic, cornstarch and like polysaccharides; water; etc.

Furthermore, flavors, colorants, acidulants, preservatives and other components that are ordinarily added to foods, beverages or medicines may be added. It is also possible to suitably add aspartame, sucralose, acesulfame potassium, saccharin or salts thereof (sodium saccharin, calcium saccharin, etc.) and like artificial sweeteners; or licorice extract, amacha extract (extract from leaf of *Hydrangea macrophylla* var. *thunbergil*), brazzein, neohesperidine dihydrochalcone, serendipity berry extract (monellin), tenryocha extract and like natural sweeteners.

The total amount of rebaudioside A and mogroside V, or the total amount of rebaudioside A, mogroside V and thaumatin in the sweetener is suitably adjusted so that it falls within the range of 0:1 to 100 weight %.

(I-2) Composition Orally Administered or Used in the Oral Cavity

The composition orally administered or used for the oral cavity of the present invention is a composition that has a sweet taste and contains rebaudioside A and. mogroside V at a weight ratio of 95:5 to 60:40. The compounding ratio of rebaudioside A to mogroside V is preferably 94:6 to 75:25 (weight ratio), and more preferably 90:10 to 75:25 (weight ratio).

The composition targeted by the present invention is a composition that is orally administered or used for the oral cavity that needs sweetness. Examples of such compositions include foods and beverages; orally administered medicines; medicines for the oral cavity; and oral care products such as dentifrices and mouthwashes (including medicines or quasi drugs). Among these, foods and beverages are preferable.

Specific examples of foods and beverages include carbonated beverages, fruit-juice beverages, coffee beverages, black tea beverages, lactic acid beverages, lactic acid bacterium beverages, soft drinks, milk beverages, alcoholic beverages and like beverages; okaki (small rice cracker), senbei (rice cracker), okoshi (dry cake made of rice or millet and starch syrup), manju (steamed azuki bean jam-filled bun), candy and other various Japanese sweets; cookies, biscuits, crackers, pies, sponge cakes, kasutera (Castilla cakes), doughnuts, waffles, butter cream, custard cream, cream puffs, chocolate, chocolate confectioneries, caramel candies, jelly, pancakes, breads and other Western-style confectioneries; chewing gum, bubble gum and like gums; potato chips and other various dry snacks; ice cream, popsicles, sherbet and other ice confectioneries; flour paste, peanut paste, fruit paste and other pastes; pickles; miso, powdered miso, soy sauce, powdered soy sauce, moromi, fish sauce, sauce, ketchup, mayonnaise, solid bouillon, sauces used for yakiniku, base for stew, base for soup, base for lightly pickled foods and other seasonings; yogurt, pudding, Bavarian cream and like milk products.

Specific examples of orally administered medicines include troche tablets, ampuled liquid medicines, granules, pulvis (powders), tablets, and capsules. Specific examples of medicines for the oral cavity include sprays, ointments, creams, pastes and patches. Specific examples of oral care products include liquid dentifrices, toothpastes, mouthwashes, and breath fresheners.

These compositions contain rebaudioside A and mogroside V with a compounding ratio that falls within the above-mentioned range, wherein the total content thereof is 10 ppm to 5,000 ppm. The total content of rebaudioside A and mogroside V depends on the type of composition targeted, but is preferably 25 ppm to 3,000 ppm, and more preferably 50 ppm to 2,000 ppm. It is preferable that thaumatin be added in an amount of 0.01 to 3 parts by mass, preferably 0.05 to 2 parts by mass, and more preferably 0.1 to 1 part by mass per total 100 parts by mass of rebaudioside A and mogroside V in the composition. This renders further improved sweetness to the composition.

Rebaudioside A and mogroside V, and optionally thaumatin, may be added to a composition that is orally administered or used for the oral cavity at any step or its production.

(I-3) Application of Sweetness to Compositions Orally Administered or Used for the Oral Cavity Sweetness can be applied to a composition that is orally administered or used for the oral cavity of the present invention by adding rebaudioside A and mogroside V to the compositions targeted in (I-2) so that their weight ratio (rebaudioside A to mogroside V) falls within the range of 95:5 to 60:40. The compounding ratio of rebaudioside A to mogroside V is preferably 94:6 to 75:25 (weight ratio) and more preferably 90:10 to 75:25 (weight ratio).

The amounts of rebaudioside A and mogroside V necessary to provide these compositions with excellent sweetness similar to that of sucrose vary depending on the type of composition, etc; however, the total amount of rebaudioside A and mogroside V is generally 10 ppm to 5,000 ppm, preferably 25 ppm to 3,000 ppm, and more preferably 50 ppm to 2,000 ppm.

In addition to rebaudioside A and mogroside V, thaumatin may be added. In this case, the content of thaumatin is generally 0.01 to 3 parts by mass, preferably 0.05 to 2 parts by mass, and more preferably 0.1 to 1 part by mass per total 100 parts by mass of rebaudioside A and mogroside V in the composition. By adding thaumatin, in addition to rebaudioside A and mogroside V, further improved sweetness can be applied to the objective composition that is orally administered or used for the oral cavity.

In the method for applying sweetness of the present invention, rebaudioside A and mogroside V, or rebaudioside A, mogroside V and thaumatin, may be independently added to the targeted composition that is orally administered or used for the oral cavity so that they have the above-mentioned compounding ratio. Alternatively, the sweeteners of the present invention described in (I-1) may be added to a targeted composition that is orally administered or used for the oral cavity so that the amounts of rebaudioside A, mogroside V and thaumatin correspond to the above-mentioned compounding ratio.

(II) Improvement in Sweetness Quality of Stevia Extract (II-1) Agent for Improving Taste of Stevia Extract The sweetness quality improving agent of the present invention consists of or comprises, as an active ingredient, at least one member selected from the group consisting of gentiooligosaccharides, naringins, highly branched cyclic dextrins, magnesium chloride and magnesium sulfate.

The stevia extract targeted by the sweetness quality improving agent of the present invention comprises, as a main component, steviol glycoside that is obtained by subjecting the leaves or stems of *Stevia Rebaudiana Bertoni* in the composite family to extraction using water or ethanol. Examples of commercially available products include Rebaudio J-100, Rebaudio A9-90, and Steviron TK (these are produced by Morita Kagaku Kogyo Co., Ltd.); Chrysanta 99-P and Chrysanta AX-P (these are produced by Dainippon Ink and Chemicals, Incorporated); Steviafin H and Steviafin HN2 (these are produced by Nippon Paper Chemicals Co., Ltd.);

Stevia ST-AB and Histevia 500 (these are produced by Ikeda Tohka Industries Co., Ltd.); etc.

The stevia extract targeted by the present invention includes enzyme-treated stevia obtained by transferring glucose, fructose or like saccharide to a stevia extract using α-glucosyltransferase, etc.

Gentiooligosaccharide, which is one of the active ingredients of the sweetness quality improving agent of the present invention, is one type of β-gluco-oligosaccharide. Gentiooligosaccharide is a low-calorie saccharide and is characteristically bitter. The gentiooligosaccharide used in the present invention can be produced by making β-glucosidase to act upon glucose or β-gluco-oligosaccharide; however, commercially available gentiooligosaccharide-containing syrups (for example, Gentose#45: Produced by Nihon Shokuhin Kako Co., Ltd., containing 45% gentiooligosaccharide) may also be obtained.

Gentiooligosaccharide may be used in an amount of generally 5 to 100 parts by mass, preferably 5 to 50 parts by mass, and more preferably 10 to 30 parts by mass per part by mass of stevia extract. When the content of gentiooligosaccharide is less than 5 parts by mass, a satisfactory reduction in the lingering sweetness of stevia extract cannot be obtained. In contrast, when the content of gentiooligosaccharide exceeds 100 parts by mass, the bitterness attributable to gentiooligosaccharide is unfavorably increased.

Naringin is a flavanone glucoside that is contained, in considerable amounts, in the peels of grapefruit, hassaku orange and like citrus fruits, and causes the bitterness or pungency of citrus fruits. The naringin used in the present invention can be obtained by subjecting the peels or fruit juice of citrus fruits to extraction and purification using water or ethanol; however, commercially available products such as SAN FIX NARINGIN (produced by San-Ei Gen F.F.I., Inc.) may also be obtained.

It is also possible to use enzyme-treated naringin that is obtained by adding glucose to naringin by making cyclodextrin glucosyltransferase to affect upon a mixture of naringin and dextrin.

The content of naringin is generally 0.01 to 1 part by mass, preferably 0.01 to 5 part by mass, and more preferably 0.02 to 0.2 part by mass per part by mass of stevia extract. When the content of naringin is less than 0.01 part by mass, a satisfactory reduction of the lingering sweetness of stevia extract cannot be attained; however, when it exceeds 1 part by mass, the bitterness attributable to naringin is unfavorably increased.

A highly branched cyclic dextrin is a high-molecular-weight dextrin having a molecular weight of about 30,000 to 1,000,000. The highly branched cyclic dextrin has characteristics, such as being easily dissolvable in cold water, and aging less easily than ordinary dextrins. The dextrin used in the present invention can be prepared by liquefying a starch essentially consisting of waxy corn starch using α-amylase, and then saccharifying the resulting mixture using a branching enzyme (EC2.4.1.18). However, commercially available products such as Cluster Dextrin (produced by Nihon Shokuhin Kako Co., Ltd.) are also usable.

Highly branched cyclic dextrin may be added in an amount of 0.1 to 50 parts by mass, preferably 0.5 to 30 parts by mass, and more preferably 1 to 20 parts by mass per part by mass of stevia extract. When the content of highly branched cyclic dextrin is less than 0.1 part by mass, satisfactory reduction in the lingering sweetness of stevia extract cannot be attained. When the content thereof exceeds 50 parts by mass, it becomes too powdery and is thus unfavorable.

Magnesium chloride, which is an inorganic compound, has deliquescence and is extremely easily dissolvable in water. An aqueous solution of magnesium chloride is called bittern. Magnesium sulfate, which is also an inorganic compound, has a bitter taste, a pleasant cooling sensation, and a salty taste. Magnesium sulfate is used as a laxative, etc.

Magnesium chloride and magnesium sulfate can each be used in an amount of 0.05 to 5 parts by mass, preferably 0.05 to 3 parts by mass, and more preferably 0.1 to 2 parts by mass per part by mass of stevia extract. When the content thereof is less than 0.05 part by mass, satisfactory reduction in the lingering sweetness of stevia extract cannot be attained. When the content thereof exceeds 5 parts by mass, the bitterness attributable to magnesium chloride and magnesium sulfate is unfavorably increased.

The sweetness quality improving agent of the present invention may consist of only one of the above components or may contain two or more components in combination.

By adding one or more pharmacologically acceptable carriers or carriers that may be added to foods and beverages to the active ingredients described above, the sweetness quality improving agent of the present invention may be prepared into an arbitrary form such as a powder, a granule, a tablet, a capsule and like solids; or syrup, emulation, liquid, gel and like semi-solids or liquids.

There is no limitation to the carriers as long as they do not hinder the effects of the present invention. Examples of carriers include lactose, glucose, fructose, sucrose, high-fructose corn syrup and like saccharides; sorbitol, erythritol, lactitol, maltitol, mannitol, xylitol, isomalt and like sugar alcohols; isomalto-oligosaccharide, galacto-oligosaccharide, fructo-oligosaccharide and like oligosaccharides; dextrin, cellulose, gum arabic, cornstarch and like polysaccharides; water; ethanol; etc.

To the sweetness quality improving agent of the present invention, within the range that does not hinder the effects of the present invention, sucralose, aspartame, acesulfame potassium, siraitia grosvenori extract, thaumatin, licorice, saccharin or salts thereof (sodium saccharin, calcium saccharin, etc.); neotame, alitame and like high intensity sweeteners; L-alanine and like amino acids; sodium gluconate, potassium gluconate, succinic acid and like acidulants; and dextrin, cellulose, gum arabic, cornstarch, inositol, caffeine, vitamins, colorant, and flavor may be added.

The contents of gentiooligosaccharide, naringin, highly branched cyclic dextin, magnesium chloride, and magnesium sulfate in the sweetness quality improving agent of the present invention are suitably adjusted so that the total amount thereof falls within the range of 0.1 to 100 weight %.

The sweetness quality improving agent of the present invention is formed into a solid, semi-solid or liquid preparation as described above by a known method, and used to improve the sweetness quality of various compositions that are orally administered or used for the oral cavity (foods and beverages, medicines orally administered or used for the oral cavity, quasi drugs used for the oral cavity, oral care products, etc.) that consist of or comprise stevia extract.

(II-2) Method for Improving Sweetness of Stevia Extract

The present invention provides a method for improving the sweetness quality of stevia extract.

The method can he conducted by combining stevia extract with the sweetness quality improving agent described in (II-1). In other words, the method can be conducted by making stevia extract coexist with the sweetness quality improving agent of the present invention. More specifically, the method can be conducted by adding the sweetness quality improving agent of the present invention to stevia extract or a stevia extract-containing composition that is orally administered or used for the oral cavity, or by adding stevia extract and the sweetness quality improving agent of the present invention to a composition that is orally administered or used for the oral cavity.

The composition of the present invention is a composition that is orally administered or used for the oral cavity that needs sweetness. Examples of such compositions include foods and beverages; orally administered medicines; medicines for the oral cavity; and oral care products such as dentifrices and mouthwashes (including medicines or quasi drugs). Among these, foods and beverages are preferable.

Specific examples of foods and beverages include carbonated beverages, fruit-juice beverages, coffee beverages, black tea beverages, lactic acid beverages, lactic acid bacterium beverages, soft drinks, milk beverages, alcoholic beverages and like beverages; okaki (rice cracker), senbei, okoshi (dry cake made of rice or millet and starch syrup), manju (steamed azuki bean jam-filled bun), candy and other various Japanese sweets; cookies, biscuits, crackers, pies, sponge cakes, kasutera (Castilla cakes), doughnuts, waffles, butter cream, custard cream, cream puffs, chocolate, chocolate confectioneries, caramel candy, jelly, pancakes, breads and other Western-style confectioneries; chewing gum, bubble gum and like gums; potato chips and other dry snacks; ice cream, popsicles, sherbet and other ice confectioneries; flour paste, peanut paste, fruit paste and other pastes; pickles; miso, powdered miso, soy sauce, powdered soy sauce, moromi, fish sauce, sauce, ketchup, mayonnaise, solid bouillon, sauces used for yakiniku, base for stew, base for soup, base for lightly pickled foods and other seasonings; and yogurt, pudding, Bavarian cream and like milk products.

Specific examples of orally administered medicines include troche tablets, ampuled liquid medicines, granules, pulvis (powders), tablets, and capsules. Specific examples of medicines for the oral cavity include sprays, ointments, creams, pastes and patches. Specific examples of oral care products include liquid dentifrices, toothpastes, mouthwashes, and breath fresheners.

The amount of stevia extract contained in these compositions varies depending on the type of composition, but is generally 10 ppm to 5,000 ppm, preferably 25 ppm to 3,000 ppm, and more preferably 50 to 2,000 ppm.

The sweetness quality improving agent of the present invention may be used so that the content of each active ingredient, relative to stevia extract or a stevia extract-containing composition, falls within the following ranges: Gentiooligosaccharide: generally 5 to 100 parts by mass, preferably 5 to 50 parts by mass, and more preferably 10 to 30 parts by mass per part by mass of stevia extract;

Naringin: 0.01 to 1 part by mass, preferably 0.01 to 0.5 part by mass, and more preferably 0.02 to 0.2 part by mass per part by mass of stevia extract;

Highly branched cyclic dextrin: 0.1 to 50 parts by mass, preferably 0.5 to 30 parts by mass, and more preferably 1 to 20 parts by mass per part by mass of stevia extract;

Magnesium chloride: 0.05 to 5 parts by mass, preferably 0.05 to 3 parts by mass, and more preferably 0.1 to 2 parts by mass per part by mass of stevia extract; and Magnesium sulfate: 0.05 to 5 parts by mass, preferably 0.05 to 3 parts by mass, and more preferably 0.1 to 2 parts by mass per part by mass of stevia extract.

(II-3) Stevia Extract-Containing Sweetener

One of the features of the sweetener of the present invention is that it contains stevia extract in combination with the sweetness quality improving agent of the present invention described in (II-1).

The compounding ratio of the stevia extract to the sweetness quality improving agent of the present invention in the sweetener may be selected so that the content of each component in the sweetness quality improving agent of the present invention falls within the following ranges:

Gentiooligosaccharide: generally 5 to 100 parts by mass, preferably 5 to 50 parts by mass, and more preferably 10 to 30 parts by mass per part by mass of stevia extract;

Naringin: 0.01 to 1 part by mass, preferably 0.01 to 0.5 part by mass, and more preferably 0.02 to 0.2 part by mass per part by mass of stevia extract;

Highly branched cyclic dextrin: 0.1 to 50 parts by mass, preferably 0.5 to 30 parts by mass, and more preferably 1 to 20 parts by mass per part by mass of stevia extract;

Magnesium chloride: 0.05 to 5 parts by mass, preferably 0.05 to 3 parts by mass, and more preferably 0.1 to 2 parts by mass per part by mass of stevia extract; and Magnesium sulfate: 0.05 to 5 parts by mass, preferably 0.05 to 3 parts by mass, and more preferably 0.1 to 2 parts by mass per part by mass of stevia extract.

There is no limitation to the form of the sweetener of the present invention, and the sweetener may take any form including a powder, a granule, a tablet, a capsule and like solid states; or syrup, emulsion, liquid, gel and like semi-solid or liquid states.

The sweetener of the present invention can be prepared by mixing stevia extract with the sweetness quality improving agent of the present invention so that their compounding ratio falls within the ranges mentioned above. During the preparation, depending on the form, pharmacologically acceptable carriers or carriers that may be added to foods and beverages may also be added. Examples of such carriers include lactose, glucose, fructose, sucrose, high-fructose corn syrup and like saccharides; sorbitol, erythritol, lactitol, maltitol, mannitol, xylitol, isomalt and like sugar alcohols; isomalto-oligosaccharide, galacto-oligosaccharide, fructo-oligosaccharide and like oligosaccharides; dextrin, cellulose, gum arabic, corn-starch and like polysaccharides; water; etc.

Furthermore, flavors, colorants, acidulants, preservatives and other components that are ordinarily added to foods, beverages or medicines may be added. If desired, it is also possible to add aspartame, saccharin, sucralose, acesulfame potassium and like synthetic sweeteners; or licorice extract, amacha extract, brazzein, neohesperidine dihydrochalcone, serendipity berry extract (monellin), tenryocha extract and like natural sweeteners.

The total amount of the stevia extract and the sweetness quality improving agent of the present invention in the sweetener is suitably adjusted so that it falls within the range of 0.1 to 100 weight %.

(II-4) Composition Orally Administered or Used for the Oral Cavity

The composition orally administered or used for the oral cavity of the present invention has a sweet taste and comprises stevia extract and at least one member selected from the group consisting of gentiooligosaccharides, naringins, highly branched cyclic dextrins, magnesium chloride and magnesium sulfate.

The composition targeted by the present invention is a composition that is orally administered or used for the oral cavity that needs sweetness. Examples of such compositions include foods and beverages; orally administered medicines; medicines for the oral cavity; oral care products such as dentifrices and mouthwashes (including medicines or quasi drugs) described in (II-2). Among these, foods and beverages are preferable.

The amount of stevia extract contained in these compositions varies depending on the type of composition, but is generally 0 ppm to 5,000 ppm, preferably 25 ppm to 3,000 ppm, and more preferably 50 to 2,000 ppm.

As described in (II-2), the content of each component in the composition of the present invention per part by mass of stevia extract falls within the following ranges:

Gentiooligosaccharide: 5 to 100 parts by mass, preferably 5 to 50 parts by mass, and more preferably 10 to 30 parts by mass;

Naringin: 0.01 to 1 part by mass, preferably 0.01 to 0.5 part by mass, and more preferably 0.02 to 0.2 part by mass;

Highly branched cyclic dextrin: 0.1 to 50 parts by mass, preferably 0.5 to 30 parts by mass, and more preferably 1 to 20 parts by mass;

Magnesium chloride: 0.05 to 5 parts by mass, preferably 0.05 to 3 parts by mass, and more preferably 0.1 to 2 parts by mass;

Magnesium sulfate: 0.05 to 5 parts by mass, preferably 0.05 to 3 parts by mass, and more preferably 0.1 to 2 parts by mass.

Stevia extract and gentiooligosaccharide, naringin, highly branched cyclic dextrin, magnesium chloride, magnesium sulfate, etc., may be added in any step of producing the composition that is orally administered or used for the oral cavity.

The composition of the present invention thus prepared solves the problem of the sweetness quality of stevia extract (such as bitterness, lingering sweetness, and slow sweetness expression) and eliminates lingering sweetness. Accordingly, the composition of the present invention has an excellent sweetness quality that is similar to that of sucrose.

(III) Acceleration of Sweetness Expression of Stevia Extract
(III-1) Method for Accelerating Sweetness Expression of Stevia Extract Among the problems of stevia extract relating to its sweetness quality, the present invention provides a method for improving slow sweetness expression in the oral cavity.

The method can be conducted by adding stevia extract in an amount of 200 to 6,000 parts by mass per part by mass of sweet flavor. The amount of stevia extract added is preferably 300 to 6,000 parts by mass, more preferably 400 to 6,000 parts by mass, and particularly preferably 600 to 4,000 parts by mass per part by mass of sweet flavor.

The stevia extract targeted by the present invention comprises, as a main component, steviol glycoside that is obtained by subjecting the leaves or stems of *Stevia Rebaudiana Bertoni* in the composite family to extraction using water or ethanol. Examples of commercially available products include Rebaudio J-100, Rebaudio A9-90, and Steviron TK (these are produced by Morita Kagaku Kogyo Co., Ltd.); Chrysanta 99-P and Chrysanta AX-P (these are produced by Dainippon Ink and Chemicals, Incorporated); Steviafin H and Steviafin HN2 (these are produced by Nippon Paper Chemicals Co., Ltd.); Stevia ST-AB and Histevia 500 (these are produced by Ikeda Tohka Industries Co., Ltd.); etc.

The stevia extract targeted by the present invention includes enzyme-treated stevia that is obtained by transferring glucose, fructose or a like saccharide to stevia extract using α-glucosyltransferase, etc.

The sweet flavor used in the present invention is an aroma component that is not sweet itself, but has an aroma similar to that of granulated sugar. Specific examples thereof include maltol, ethyl maltol, sotolon, cyclotene, furaneol and homofuraneol. These sweet flavors may be used singly or in combination. Among various possible combinations, it is preferable to use maltol singly or in combination with other sweet flavors. The sweet flavor may be used singly by diluting it with a solvent, or in combination with other flavors, such as a citrus-based flavor. Furthermore, minor components such as sucrose lactone that is reminiscent of brown sugar or maple syrup, and cyclotene; and natural raw materials such as molasses extract and honey extract, may also be added.

The proportion of the stevia extract to sweet flavor used to achieve the effect of the present invention, i.e., accelerating the sweetness expression of stevia extract in the oral cavity, depends on the type of the sweet flavor used, but is generally 200 to 6,000 parts by mass, preferably 300 to 6,000 parts by mass, more preferably 400 to 6,000 parts by mass, and particularly preferably 600 to 4,000 parts by mass per part of sweet flavor. When the content of stevia extract per part by mass of sweet flavor is less than 200 parts by mass, the sucrose-like aroma of the sweet flavor becomes too conspicuous and an unfavorable lingering sweetness (a remaining aftertaste) increases. In contrast, when the content of stevia extract per part by mass of sweet flavor exceeds 6,000 parts by mass, the satisfactory effect of the present invention cannot be attained.

The sweetness expression of the stevia extract in the oral cavity can be accelerated by adding sweet flavor to stevia extract itself, a sweetener that contains stevia extract as an active ingredient, or a composition that is orally administered or used for the oral cavity that has a sweet taste and contains stevia extract, with the proportion of stevia extract to sweet flavor falling within the above-described range.

The sweetener targeted by the present invention may suitably contain, in addition to stevia extract, lactose, glucose, fructose, sucrose, high-fructose corn syrup and like saccharides; sorbitol, erythritol, lactitol, maltitol, mannitol, xylitol, isomalt and like sugar alcohols; isomalto-oligosaccharide, galacto-oligosaccharide, fructo-oligosaccharide and like oligosaccharides; dextrin, cellulose, gum arabic, cornstarch and like polysaccharides; amino acid or a salt thereof; aspartame, sucralose, acesulfame potassium, neotame and like synthetic sweeteners; thaumatin, licorice extract, amacha extract, brazzein, serendipity extract (monellin), tenryocha extract and like natural sweeteners.

The composition targeted by the present invention is a composition that is orally administered or used for the oral cavity that contains stevia extract. Examples of such compositions include foods and beverages; orally administered medicines; medicines for the oral cavity; and dentifrices, mouthwashes and like oral care products (including medicines and quasi drugs). Among these, foods and beverages are preferable, and beverages are particularly preferable.

Specific examples of foods and beverages include carbonated beverages, fruit-juice beverages, coffee beverages, black tea beverages, lactic acid beverages, lactic acid bacterium beverages, soft drinks, milk beverages, alcoholic beverages and like beverages; okaki (small rice cracker), senbei (rice cracker), okoshi (dry cake made of rice or millet and starch syrup), manju (steamed azuki bean jam-filled bun), candy and other various Japanese sweets; cookies, biscuits, crackers, pies, sponge cakes, kasutera (Castilla cakes), doughnuts, waffles, butter cream, custard cream, cream puffs, chocolate, chocolate confectioneries, caramel candy, jelly, pancakes, breads and other Western-style confectioneries; chewing gum, bubble gum and like gums; potato chips and other dry snacks; ice cream, popsicles, sherbet and other ice confectioneries; flour paste, peanut paste, fruit paste and other pastes; pickles; miso, powdered miso, soy sauce, powdered soy sauce, moromi, fish sauce, sauce, ketchup, mayonnaise, solid bouillon, sauces used for yakiniku, base for stew, base for soup, base for lightly-picked foods and other seasonings; yogurt, pudding, Bavarian cream and like milk products.

Specific examples of orally administered medicines include troche tablets, ampuled liquid medicines, granules, pulvis (powders), tablets, and capsules Specific examples of medicines for the oral cavity include sprays, ointments, creams, pastes and patches. Specific examples of oral care products include liquid dentifrices, toothpastes, mouthwashes, and breath fresheners.

Stevia extract and sweet flavor may be added at the same time or individually in the process of producing these compositions.

The amount of stevia extract added to these compositions depends on the type of composition, etc., but is generally 10 ppm to 5,000 ppm, preferably 25 ppm to 3,000 ppm, and more preferably 50 ppm to 2,000 ppm. To stevia extract of such amounts, sweet flavor may be added so that their proportion falls within the above-mentioned ranges. More specifically, for example, when the amount of stevia extract added to the composition is 600 ppm, the amount of sweet flavor added is generally 0.1 to 3 ppm, and preferably 0.1 to 2 ppm.

(III-2) Sweetener

The sweetener of the present invention contains stevia extract and the sweet flavor described earlier. One of the features of the sweetener of the present invention is that it contains 200 to 6,000 parts by mass of stevia extract per part by mass of sweet flavor. The amount of stevia extract per part by mass of sweet flavor is preferably 300 to 6,000 parts by mass, more preferably 400 to 6,000 parts by mass, and particularly preferably 600 to 4,000 parts by mass.

There is no limitation to the form of the sweetener of the present invention, and the sweetener may take any form including a powder, a granule, a tablet, a capsule and like solid states; or syrup, emulsion, liquid, gel and like semi-solid or liquid states.

The sweetener of the present invention can be prepared by mixing stevia extract and sweet flavor so that their compounding ratio falls within the range described above. During the preparation, depending on the form, pharmacologically acceptable carriers or carriers that may be added to foods and beverages may also be added. Examples of such carriers include lactose, glucose, fructose, sucrose, high-fructose corn syrup and like saccharides; sorbitol, erythritol, lactitol, maltitol, mannitol, xylitol, isomalt and like sugar alcohols; isomalto-oligosaccharide, galacto-oligosaccharide, fructo-oligosaccharide and like oligosaccharides; dextrin, cellulose, gum arabic, cornstarch and like polysaccharides; water; etc.

Furthermore, flavors, colorants, acidulants, preservatives and other components that are ordinarily added to foods, beverages or medicines may be added. If desired, it is also possible to add aspartame, sucralose, acesulfame potassium and like artificial sweeteners; or licorice extract, amacha extract, brazzein, neohesperidine dihydrochalcone, serendipity berry extract (monellin), tenryocha extract and like natural sweeteners.

The total amount of sweet flavor and stevia extract in the sweetener is suitably adjusted so as to fall within the range of 0.1 to 100% by mass.

(III-3) Composition Orally Administered or Used for the Oral Cavity

The composition orally administered or used for the oral cavity of the present invention has a sweet taste and contains stevia extract and sweet flavor as described in (III-1), wherein the amount of the stevia extract is 200 to 6,000 parts by mass per part by mass of sweet flavor. The amount of stevia extract per part by mass of sweet flavor is preferably 300 to 6,000 parts by mass, more preferably 400 to 6,000 parts by mass, and particularly preferably 600 to 4,000 parts by mass.

The composition targeted by the present invention is a composition that is orally administered or used for the oral cavity that has sweetness. Examples of such compositions include those mentioned in (III-1), such as foods and beverages; orally administered medicines; medicines for the oral cavity; dentifrices, mouthwashes and like oral care products (including medicines or quasi drugs). Among these, foods and beverages are preferable.

The content of stevia extract in these compositions depends on the type of composition, but is generally 10 ppm to 5,000 ppm, preferably 25 ppm to 3,000 ppm, and more preferably 50 ppm to 2,000 ppm. To stevia extract of such amounts, sweet flavor may be added so that their compounding ratio falls within the above-mentioned ranges. More specifically, for example, when the amount of stevia extract added to the composition is 600 ppm, the amount of sweet flavor added is generally 0.1 to 3 ppm, and preferably 0.1 to 2 ppm.

The stevia extract and sweet flavor may be added in any step of producing a composition that is orally administered or used for the oral cavity.

The composition of the present invention thus prepared solves the problem of the sweetness quality in stevia extract, i.e., slow sweetness expression, and provides an excellent sweetness quality similar to that of sucrose.

EXAMPLES

The present invention is explained in detail below with reference to the Examples described below. However, the scope of the present invention is not limited to these Examples. The term "parts" indicates "parts by mass" and "%" indicates "% by mass" unless otherwise specified. The "*" symbol in the specification indicates a product of San-Ei Gen F.F.I., Inc., and "†" indicates a registered trademark of San-Ei Gen F.F.I., Inc.

Unless otherwise specified, in the Examples below, "stevia extract" means "stevia extract (Rebaudio J-100, produced by Morita Kagaku Kogyo Co., Ltd.) that contains 95% by mass of rebaudioside A, and "siraitia grosvenorii extract" means siraitia grosvenori extract that contains 15% by mass of mogroside V. The siraitia grosvenorii extract was prepared by freeze-drying a water extract of dried siraitia grosvenorii. Examples 1 and 2 were conducted using the "stevia extract" and "siraitia grosvenori extract" described above as the "rebaudioside A" and "mogroside V" respectively. In Examples 1 and 2, the compounding ratios and amounts of rebaudioside A and mogroside V are calculated based on the amount of rebaudioside A itself and that of mogroside V itself.

(I) Improvement in Sweetness Quality of Rebaudioside A

Example 1

Evaluation of Sweetness Quality (Without Thaumatin)

(1) Degree of Sweetness (Intensity of Sweetness) of Rebaudioside A and Mogroside V The degree of sweetness of rebaudioside A and that of mogroside V depends on the pH. Table 1 shows the concentrations (%) of rebaudioside A and mogroside V in aqueous solutions (pH3, pH4.5 and pH7) prepared by dissolving each of rebaudioside A or mogroside V singly into water to attain the same degree of sweetness (intensity of sweetness) as that of a 5% aqueous sucrose solution. Citric acid and trisodium citrate were used to prepare pH3 and pH4.5 solutions, and sodium bicarbonate was used to prepare pH7 solutions.

TABLE 1

Concentrations of rebaudioside A and mogroside V having the same degree of sweetness as that of a 5% aqueous sugar solution

|  | pH 3 | pH 4.5 | pH 7 |
|---|---|---|---|
| Rebaudioside A singly | 0.0228% | 0.0219% | 0.02% |
| Mogroside V singly | 0.03% | 0.03% | 0.0255% |

(2) Preparation of Aqueous Test Solutions

Rebaudioside A and mogroside V having the degrees of sweetness described above were mixed at the ratios (weight ratios) shown in Table 2. Water was added to the mixture so as to obtain a degree of sweetness (intensity of sweetness) similar to that of a 5% aqueous sucrose solution, preparing eight types of aqueous solutions containing rebaudioside A and/or mogroside V. The pH of each aqueous solution was adjusted to pH3 or pH4.5 using citric acid and trisodium citrate, or to pH7 using sodium bicarbonate.

(3) Evaluation of Sweetness Quality

Ten panelists were asked to evaluate the sweetness quality of the aqueous solutions that were prepared above. Specifically, the sweetness quality of an aqueous solution (Control) containing only rebaudioside A (i.e., rebaudioside A:mogroside V=100:0) was set to 0 points. As the sweetness quality of an aqueous test solution came closer to that of a 5% aqueous sucrose solution, points were added one by one, and when the sweetness quality became most similar to that of a 5% aqueous sucrose solution, the sweetness quality was given 5 points. In the same manner, using the sweetness quality of the Control as reference (0 points), the sweetness quality score was lowered one point at a time as the sweetness quality of an aqueous test solution became further from that of a 5% aqueous sucrose solution. The aqueous test solution having a sweetness quality that was the furthest from that of the 5% aqueous sucrose solution was given −5 points. Table 2 shows the average scores of the ten panelists.

TABLE 2

| Rebaudioside A:Mogroside V (Weight Ratio) | pH 3 | pH 4.5 | pH 7 |
|---|---|---|---|
| 100:0 (Control) | 0 | 0 | 0 |
| 87:13 | +2.2 | +1.8 | +2.0 |
| 75:25 | +1.5 | +1.4 | +2.0 |
| 64:36 | +0.3 | +0.3 | −0.1 |
| 53:47 | −0.7 | −0.2 | −0.5 |
| 43:57 | −1.3 | −0.9 | −1.5 |
| 16:84 | −3.4 | −2.8 | −3.1 |
| 0:100 | −4.0 | −3.4 | −3.8 |

As seen by the results, the sweetness quality of rebaudioside A improved and became closer to that of sucrose by adding 36 parts or less of mogroside V per 64 parts of rebaudioside A. In contrast, the sweetness quality of rebaudioside A started becoming further from that of sucrose when 47 parts or more at mogroside V was added per 53 parts of rebaudioside A.

Example 2

Evaluation of Sweetness Quality (With Thaumatin Added)

(1) Preparation of Aqueous Test Solutions

Rebaudioside A and mogroside V were mixed in the same manner as in Example 1 with the compounding ratio (weight ratio) shown in Table 3. Water was added to the mixture so as to obtain a degree of sweetness (intensity of sweetness) similar to that of a 5% aqueous sucrose solution, and eight types of aqueous solutions containing rebaudioside A and/or mogroside V were prepared. Among these aqueous test solutions, thaumatin was added to each aqueous solution, except for an aqueous solution consisting of 100 parts by mass of rebaudioside A (Control, rebaudioside A:mogroside V=100:0), so that its concentration became 1 ppm. The pH of each aqueous solution was adjusted to 3 and 4.5 using citric acid and trisodium citrate, and to 7 using sodium bicarbonate.

(2) Evaluation of Sweetness Quality

In the same manner as in Example 1, ten panelists were asked to evaluate the sweetness quality of each of the aqueous test solutions prepared above.

TABLE 3

| Rebaudioside A:Mogroside V (Weight Ratio) | Thaumatin Added | pH 3 | pH 4.5 | pH 7 |
|---|---|---|---|---|
| 100:0 (Control) | — | 0 | 0 | 0 |
| 87:13 | 1 ppm | +3.5 | +3.4 | +3.4 |
| 75:25 | 1 ppm | +4.0 | +2.2 | +2.7 |
| 64:36 | 1 ppm | +1.2 | +1.1 | +2.4 |
| 53:47 | 1 ppm | −0.6 | +0.4 | +0.6 |
| 43:57 | 1 ppm | −1.1 | −1.1 | −0.6 |
| 16:84 | 1 ppm | −2.0 | −2.1 | −1.8 |
| 0:100 | 1 ppm | −2.8 | −2.9 | −2.2 |

As seen by the results, the sweetness quality of rebaudioside A improved and became closer to that of sucrose by adding 47 parts or less of mogroside V per 53 parts of rebaudioside A, and preferably 36 parts or less of mogroside V per 64 parts of rebaudioside A, in the presence of 1 ppm thaumatin. The results also indicate that the sweetness quality started becoming further from that of sucrose when 57 parts or more of mogroside V was added per 43 parts of rebaudioside A. A comparison of the results of Example 1 (Table 2) and those shown in Table 3 also it clear that the sweetness quality was further improved and became closer to that of sucrose when mogroside V and rebaudioside A were used in combination with thaumatin.

Examples 3 and 4

Sweeteners Containing Rebaudioside A

According to the formulae shown in Table 4, various components were mixed to prepare three types of sweeteners (Comparative Example, and Examples 3 and 4). The proportion of rebaudioside A to mogroside V contained in the sweeteners of Examples 3 and 4 was 86:14 (weight ratio). These sweeteners were adjusted to have a degree of sweetness (sweetness intensity relative to sucrose) of about 100 times that of sucrose.

TABLE 4

|  | Comparative Example | Example 3 | Example 4 |
|---|---|---|---|
| Isomalt | 58.0 | 22.2 | 22.1 |
| Stevia Extract | 42.0 | 37.8 | 37.8 |
| (Rebaudioside A) | (39.9) | (35.91) | (35.91) |
| Siraitia Grosvenorii Extract (Mogroside V) | — | 40.0 (6.00) | 40.0 (6.00) |
| Thaumatin | — | — | 0.1 |
| Total | 100.0 | 100.0 | 100.0 |

(Unit: Part by mass)

Each of the obtained sweeteners (0.05 g) was dissolved in water (100 mL). Ten panelists were asked to evaluate the taste (speed of sweetness expression, lingering sweetness, and presence or absence of bitterness) of the test solutions. Table 5 shows the results of the evaluation. The ten panelists were also asked to compare the taste (speed of sweetness expression, lingering sweetness, and presence or absence of bitterness) with that of a Control solution obtained by dissolving 5 g of sucrose in 100 mL of water (a 5% aqueous sucrose solution: Control). Table 5 shows the results.

TABLE 5

| Comparative Example | Slower sweetness expression than Control. Lingering sweetness (remaining aftertaste) and distinctive bitterness. |
|---|---|
| Example 3 | Compared to the Comparative Example, the sweetness expression was faster and became closer to that of sugar. The lingering sweetness observed in the Comparative Example was reduced. The bitterness observed in the Comparative Example was reduced (bitterness was masked). |
| Example 4 | Compared to the Comparative Example, the sweetness expression was faster and became closer to that of sugar. The lingering sweetness observed in the Comparative Example was reduced, and the aftertaste was improved. The bitterness observed in the Comparative Example did not exist (bitterness was masked). |

The results indicate that, by using rebaudioside A together with mogroside V, the speed of sweetness expression felt in the oral cavity became closer to that of sucrose, and the lingering sweetness was reduced. By also using thaumatin in combination with rebaudioside A and mogroside V, the lingering sweetness could be further reduced and the bitterness was masked, so that the sweetness quality became closer to that of sucrose.

Example 5

Coffee Beverages (1) Preparation of Sweeteners

According to the formulae shown in Table 6, five types of sweeteners (Control, Comparative Example, and Examples 5-1 to 5-3) were prepared. The proportion of rebaudioside A to mogroside V in the sweeteners of Examples 5-1 to 5-3 was adjusted to 86:14 (weight ratio).

TABLE 6

| Sweeteners | Control | Comparative Example | Example 5-1 | Example 5-2 | Example 5-3 |
|---|---|---|---|---|---|
| Sugar | 5.0 | — | — | — | 1.7 |
| Stevia Extract (Rebaudioside A) | — | 0.021 (0.01995) | 0.019 (0.01805) | 0.019 (0.01805) | 0.013 (0.01235) |
| Siraitia Grosvenorii Extract (Mogroside V) | — (—) | — (—) | 0.02 (0.003) | 0.02 (0.003) | 0.013 (0.00195) |
| Thaumatin-containing preparation (Thaumatin) | — (—) | — (—) | — (—) | 0.03 (0.000045) | 0.03 (0.000045) |

(Unit: Part by mass)

*Thaumatin-containing preparation: A preparation that contained 0.15% of thaumatin (NEO SAN MARUKU† AG: produced by San-Ei Gen F.F.I., Inc.)

(2) Preparation or Coffee Beverages

According to the formulae shown in Table 7, powder mixtures of the sweeteners (Table 6) and an emulsifier were added to water. Each mixture was dissolved while stirring at 80° C. for 10 minutes and then cooled to room temperature. Cow's milk, sodium bicarbonate, and coffee were sequentially added to each mixture. The pH was adjusted to 6.8, and water was added thereto to make the total amount 100 parts. The resulting mixtures were heated to 75° C., and homogenized using a homogenizer. Coffee flavor was added to the mixtures. After being placed in a container, each mixture was subjected to retort-sterilization at 121° C. for 20 minutes.

TABLE 7

| | (Unit: Part by Mass) |
|---|---|
| Coffee (L = 20, Brix = 3) | 41.0 |
| Cow's milk | 10.0 |
| Sweeteners (Control, Comparative Example, and Examples 5-1 to 5-3) | Table 6 |
| Emulsifier (Homogen† No. 1379*) | 0.14 |
| pH Controlling agent (Sodium bicarbonate) | q.s. (pH6.8) |
| Flavor (Coffee Flavor No. 90154*) | 0.01 |
| Water | Balance |
| Total | 100.0 |

(3) Evaluation of Coffee Beverages (Sensory Evaluation)

Ten panelists were asked to taste the coffee beverages obtained above (depending on the sweeteners used, the coffee beverages were categorized into Control, Comparative Example, Examples 5-1, 5-2, and 5-3) to evaluate their taste (speed of sweetness expression, lingering sweetness, and presence or absence of bitterness). Table 8 shows the evaluation results. The evaluation was conducted by using the taste (speed of sweetness expression, lingering sweetness, and presence or absence of bitterness) of a coffee beverage prepared using only sucrose as the sweetener (Control) as reference and comparing the taste of each test sample with that of the Control.

TABLE 8

| Coffee Beverages | Evaluations |
|---|---|
| Comparative Example | Slower sweetness expression than the Control. Lingering sweetness and distinctive bitterness. |
| Example 5-1 | Compared to the Comparative Example, the sweetness expression was faster and became closer to that of sugar. The lingering sweetness observed in the Comparative Example was reduced. The bitterness observed in the Comparative Example was reduced (bitterness was masked). |
| Example 5-2 | Compared to the Comparative Example, the sweetness expression was faster and became closer to that of sugar. The lingering sweetness observed in the Comparative Example was reduced, and the aftertaste was improved. The bitterness observed in the Comparative Example did not exist (bitterness was masked). |
| Example 5-3 | The sweetness expression was as fast as that of the Control. Lingering sweetness and bitterness did not exist and the sweetness quality was almost the same as that of the Control. |

Example 6

Beverages Containing Orange Juice (1) Preparation of Sweeteners

According to the formulae shown in Table 9, five types of sweeteners (Control, and Examples 6-1 to 6-4) were prepared. The proportion of rebaudioside A to mogroside V in the sweeteners of Examples 6-1 to 6-4 was adjusted to 79:21 (weight ratio).

TABLE 9

| | Sweeteners (Unit: Part by mass) | | | | |
|---|---|---|---|---|---|
| | Control | Example 6-1 | Example 6-2 | Example 6-3 | Example 6-4 |
| Sugar | 7.0 | — | — | 3.5 | 3.5 |
| Stevia Extract (Rebaudioside A) | — (—) | 0.033 (0.03135) | 0.033 (0.03135) | 0.013 (0.01235) | 0.013 (0.01235) |
| Siraitia Grosvenorii Extract (Mogroside V) | — (—) | 0.056 (0.0084) | 0.056 (0.0084) | 0.02 (0.003) | 0.02 (0.003) |
| Thaumatin-containing preparation (Thaumatin) | — (—) | — (—) | 0.05 (0.000075) | — (—) | 0.05 (0.000075) |

*Thaumatin-containing preparation: A preparation that contained 0.15% of thaumatin (NEO SAN MARUKU† AG: produced by San-Ei Gen F.F.I., Inc.)

(2) Preparation of Beverages Containing Orange Juice

According to the formulae shown in Table 10, 5-fold concentrated orange juice, citric acid (anhydrous) fine particles, trisodium citrate fine particles and each of the sweeteners of Table 9 were mixed. The resulting mixtures were dissolved in water while heating and stirring. After heating the mixtures to 93° C., orange flavor was added thereto, water was added to make the total amount 100 parts, and each of the resulting mixtures was placed in a container.

TABLE 10

| | (Unit: Part by mass) |
|---|---|
| 5-Fold concentrated orange juice | 6.6 |
| Citric acid (anhydrous) fine particles* | 0.15 |
| Trisodium citrate fine particles* | 0.03 |
| Sweeteners (Control, and Examples 6-1 to 6-4) | Table 9 |
| Flavor (Orange Flavor No. 2410*) | 0.10 |
| Water | Balance |
| Total | 100.0 |

(3) Evaluation of Beverages Containing Orange Juice (Sensory Evaluation)

Twelve panelists were asked to taste the obtained beverages containing orange juice (depending on the sweeteners used, the beverages containing orange juice were categorized into Control, Comparative Example, and Examples 6-1, 6-2, 6-3, and 6-4) to evaluate their taste (speed of sweetness expression, lingering sweetness, and presence or absence of bitterness). Table 11 shows the evaluation results. The evaluation was conducted using the taste (speed of sweetness expression, lingering sweetness, and presence or absence of bitterness) of a beverage containing orange juice prepared using only sucrose as the sweetener (Control) as reference and comparing the taste of each test sample with that of the Control.

TABLE 11

| Beverages Containing Orange Juice | Evaluations |
|---|---|
| Example 6-1 | Fast sweetness expression similar to that of the Control, but a slightly bitter aftertaste. |
| Example 6-2 | Fast sweetness expression similar to that of the Control. The bitterness observed in Example 6-1 was reduced, and the aftertaste was improved. |

TABLE 11-continued

| Beverages Containing Orange Juice | Evaluations |
|---|---|
| Example 6-3 | The sweetness expression was as fast as that of the Control. The sweet quality was similar to that of Example 6-2, but there was a slightly bitter aftertaste. |
| Example 6-4 | The sweetness expression was as fast as that of the Control. The sweetness quality was almost the same as that of the Control. |

Example 7

Apply Jelly (1) Preparation of Sweeteners

According to the formulae shown in Table 12, four types of sweeteners (Control, Comparative Example, and Examples 7-1 and 7-2) were prepared. The proportion of rebaudioside A to mogroside V in the sweeteners of Examples 7-1 and 7-2 was adjusted to 89:11 (weight ratio).

TABLE 12

(Unit: Part by mass)

|  | Control | Comparative Example | Example 7-1 | Example 7-2 |
|---|---|---|---|---|
| Sugar | 5.0 | 2.0 | 2.0 | 2.0 |
| Stevia Extract (Rebaudioside A) | — | 0.0135 (0.012825) | 0.012 (0.0114) | 0.012 (0.0114) |
| Siraitia Grosvenorii Extract (Mogroside V) | — | — (—) | 0.009 (0.00135) | 0.009 (0.00135) |
| Thaumatin-containing preparation (Thaumatin) | — | — (—) | — (—) | 0.05 (0.000075) |

* Thaumatin-containing preparation: A preparation that contained 0.15% of thaumatin (NEO SAN MARUKU† AG: produced by San-Ei Gen F.F.I., Inc.)

(2) Preparation of Apple Jelly

According to the formulae shown in Table 13, a high-fructose corn syrup was added to water, then a powder mixture of each of the sweeteners of Table 12 and a gelling agent was added while stirring, and the resulting mixture was dissolved while stirring at 80° C. for 10 minutes. Five-fold concentrated apple juice (clarified), trisodium citrate fine particles, citric acid (anhydrous) medium-size particles and apple flavor were added to the mixture, and water was added to make the total amount 100 parts. Each of the resulting mixtures was placed in a container, and subjected to sterilization at 85° C. for 30 minutes.

TABLE 13

(Unit: Part by mass)

| | |
|---|---|
| High-fructose corn syrup | 15.0 |
| Sweeteners (Control, Comparative Example, and Examples 7-1 and 7-2) | Table 12 |
| Five-fold concentrated apple juice (clarified) | 4.2 |
| Gelling agent (GEL UP† WM-100*) | 1 |
| Citric acid (anhydrous) medium-size particles | 0.25 |
| Trisodium citrate fine particles | 0.03 |
| Flavor (Apple Flavor No. 2414*) | 0.1 |
| Water | Balance |
| Total | 100.0 |

(3) Evaluation of Apple Jelly (Sensory Evaluation)

Twelve panelists were asked to taste the obtained apple jelly (depending on the sweeteners used, the apple jelly was categorized into Control, Comparative Example, and Examples 7-1 and 7-2) to evaluate the taste (lingering sweetness, rough taste (presence of bitterness and/or astringency)). Table 14 shows the results. The evaluation was conducted using the taste (lingering sweetness, and presence of rough taste) of an apple jelly prepared using only sucrose and a high-fructose corn syrup as sweeteners (Control) as reference and comparing the taste of each test sample with that of the Control.

TABLE 14

| Apple Jelly | Evaluations |
|---|---|
| Comparative Example | There was a sweet aftertaste, and a rough aftertaste (bitterness and astringency) |
| Example 7-1 | The sweet aftertaste observed in the Comparative Example was reduced. There was a rough aftertaste (bitterness and astringency). |
| Example 7-2 | The sweet aftertaste and rough aftertaste observed in the Comparative Example and Example 7-1 were reduced. The sweet quality was almost the same as that of the Control (sugar). |

Example 8

Seasonings (Seasonings for Preparing Lightly Pickled Foods)

(1) Preparation of Sweeteners

According to the formulae shown in Table 15, three types of sweeteners (Control, and Examples 8-1 and 8-2) were prepared. The proportion of rebaudioside A to mogroside V in the sweeteners of Examples 8-1 and 8-2 was adjusted to 94:6 (weight ratio).

TABLE 15

(Unit: Part by mass)

| | Control | Example 8-1 | Example 8-2 |
|---|---|---|---|
| High-fructose corn syrup | 13.0 | — | — |
| Stevia Extract (Rebaudioside A) | — | 0.073 (0.06935) | 0.073 (0.06935) |
| Siraitia Grosvenorii Extract (Mogroside V) | — | 0.032 (0.0048) | 0.032 (0.0048) |
| Thaumatin-containing preparation (Thaumatin) | — | — (—) | 0.05 (0.000075) |

* Thaumatin-containing preparation: A preparation that contained 0.15% of thaumatin (NEO SAN MARUKU† AG: produced by San-Ei Gen F.F.I., Inc.)

(2) Preparation of Seasonings (Seasonings for Preparing Lightly Pickled Foods)

According to the formulae shown in Table 16, each of the sweeteners of Table 15 and other components were added to water, followed by stirring and dissolving the resulting mixture to produce seasonings for preparing lightly pickled foods.

TABLE 16

(Unit: Part by mass)

| | |
|---|---|
| Sweetener | Table 15 |
| Light soy sauce | 5.0 |
| Fermented alcohol beverage (Acidity of 4.2%) | 12.0 |

TABLE 16-continued (Unit: Part by mass)

| | |
|---|---|
| Dietary salt | 6.0 |
| L-Sodium glutamate | 0.5 |
| Disodium succinate | 0.2 |
| Seasoning (SAN-LIKE TASTE BASE A*) | 0.4 |
| Flavor(SAN-AROMA RED PEPPER SV-3541(N)*) | 0.004 |
| Water | Balance |
| Total | 100.0 |

(3) Evaluation (Sensory Evaluation) for Seasonings (Seasonings for Preparing Lightly Pickled Foods)

Daikon radish was soaked in each of the obtained seasonings (depending on the sweetener used, they are categorized into Control, and Examples 8-1 and 8-2) in the proportion of 1:1 (weight ratio) daikon radish to seasoning. After one day of soaking, the daikon radish (lightly pickled daikon radish) was removed from the seasoning. Ten panelists were asked to taste the resulting pickles. Table 17 shows the evaluation results. The evaluation was conducted using daikon radish (lightly pickled daikon radish) soaked in a seasoning prepared using only a high-fructose corn syrup as the sweetener (Control) as reference, and the taste of each test sample was compared with that of the Control.

TABLE 17

| Seasoning | Evaluation of the taste of daikon radish soaked in each seasoning (lightly pickled daikon radish) |
|---|---|
| Example 8-1 | The soy sauce flavor was improved compared to that of the Control (seasoning). There was a slightly rough aftertaste. |
| Example 8-2 | The rough aftertaste observed in Example 8-1 had disappeared. There was an increased salty taste. |

As is clear from the results of Examples 5 to 8, the use of a sweetener that contains rebaudioside A and mogroside V at a weight ratio of 75:25 to 94:6 can render an excellent sweetness, i.e., a sweetness quality similar to that of sucrose, to foods, beverages and like orally consumed compositions. It was also confirmed that, by adding thaumatin to a sweetener having the above-mentioned ratio, a more improved sweetness can be obtained that is closer to the sweetness quality of sucrose.

(II) Improvement in Sweetness Quality of Stevia Extract

Examples 9 to 13

Zero-Calorie Carbonated Beverages (I) Preparation of Carbonated Beverages

According to the formulae shown in Table 18, lemon juice, stevia extract, citric acid (anhydrous), trisodium citrate, colorant, and lemon flavoring, in addition to at least one member selected from the group consisting of gentiooligosaccharides, naringins, highly branched cyclic dextrins, magnesium chloride and magnesium sulfate, were added to water and dissolved therein, to prepare syrups for carbonated beverages.

After cooling, 80 mL of carbonated water was added to 20 mL of syrup, making the total amount 100 mL. Each of the resulting liquids was placed in a container and sterilized at 70° C. for 20 minutes, to prepare a carbonated beverage.

TABLE 18

(Part by mass)

| | | Example | | | | | Comp. Ex. |
|---|---|---|---|---|---|---|---|
| | | 9 | 10 | 11 | 12 | 13 | |
| Lemon juice | | 4.2 | 4.2 | 4.2 | 4.2 | 4.2 | 4.2 |
| *Stevia* extract | | 0.033 | 0.033 | 0.033 | 0.033 | 0.033 | 0.033 |
| Citric acid (anhydrous) | | 0.2 | 0.2 | 0.2 | 0.2 | 0.2 | 0.2 |
| Trisodium citrate | | 0.1 | 0.1 | 0.1 | 0.1 | 0.1 | 0.1 |
| Additives | Gentiooligosaccharide[1] | 0.4 | — | — | — | — | — |
| | Naringin | — | 0.0025 | — | — | — | — |
| | Magnesium chloride | — | — | 0.05 | — | — | — |
| | Magnesium sulfate | — | — | — | 0.05 | — | — |
| | Highly branched cyclic dextrin[2] | — | — | — | — | 0.07 | — |
| Colorant (SAN YELLOW† No. 2 SFU*) | | 0.009 | 0.009 | 0.009 | 0.009 | 0.009 | 0.009 |
| Flavor (Lemon flavor) | | 0.1 | 0.1 | 0.1 | 0.1 | 0.1 | 0.1 |
| Water | | Balance | Balance | Balance | Balance | Balance | Balance |
| Total | | 20.0 | 20.0 | 20.0 | 20.0 | 20.0 | 20.0 |

[1]Gentose#45: Produced by Nihon Shokuhin Kako Co., Ltd., containing 45% or more gentiooligosaccharide.
[2]Cluster Dextrin: Produced by Nihon Shokuhin Kako Co., Ltd.

(2) Evaluation Results

Ten panelists were asked to taste each carbonated beverage prepared above. Table 19 shows the evaluation results.

TABLE 19

| Carbonated Beverage | Additive Used | Sensory Evaluation Result |
|---|---|---|
| Comparative Example | — | There was a sweet aftertaste. There was insufficient richness (body), and the taste was not delicious. |
| Example 9 | Gentiooligosaccharide[1] | The sweet aftertaste observed in the Comparative Example was reduced. Richness was added to the sweetness. |
| Example 10 | Naringin | The sweet aftertaste observed in the Comparative Example was reduced. The juiciness was increased. |
| Example 11 | Magnesium chloride | The sweet aftertaste observed in the Comparative Example was reduced. There was a refreshing aftertaste. |

TABLE 19-continued

| Carbonated Beverage | Additive Used | Sensory Evaluation Result |
|---|---|---|
| Example 12 | Magnesium sulfate | The sweet aftertaste observed in the Comparative Example was reduced. There was an increased sparkling effect of the carbonated beverages. |
| Example 13 | Highly branched cyclic dextrin[2] | The sweet aftertaste observed in the Comparative Example was reduced. Richness was added to the sweetness, and there was a refreshing aftertaste. |

[1]Gentose#45: Produced by Nihon Shokuhin Kako Co., Ltd., containing 45% or more gentiooligosaccharide.
[2]Cluster Dextrin: Produced by Nihon Shokuhin Kako Co., Ltd.

As described above, by adding at least one member selected from the group consisting of gentiooligosaccharides, naringins, highly branched cyclic dextrins, magnesium chloride and magnesium sulfate to a stevia extract-containing carbonated beverage, the lingering sweetness of the stevia extract can be reduced and the richness (body), juiciness, and sparkling effect of carbonated beverages can be increased.

Example 14

Aqueous solutions containing various sweeteners (stevia extract, siraitia grosvenori extract, licorice extract, thaumatin, aspartame, and neotame) in the concentrations shown in Table 20 were prepared. The concentration of each sweetener was adjusted so as to exhibit the same degree of sweetness as that of a 6% aqueous sucrose solution.

TABLE 20

| Sweetener | Concentration (%) |
|---|---|
| Stevia extract | 0.03 |
| Siraitia grosvenorii extracts[1] | 0.05 |
| Licorice extract[2] | 0.05 |
| Thaumatin | 0.0024 |
| Aspartame | 0.038 |
| Neotame[3] | 0.0008 |

[1]LUO HAN GUO CONCENTRATE EXTRACT POWDER (containing 15% mogroside V; Produced by San-Ei Gen F.F.I., Inc.)
[2]Licotin P1 (produced by Ikeda Tohka Industries Co., Ltd.)
[3]Mirasee (containing 2% neotame, produced by Dainippon Sumitomo Pharma Co., Ltd.)

Subsequently, various additives (gentiooligosaccharide, naringin, highly branched cyclic dextrin, magnesium chloride, and magnesium sulfate) were added to each of the above aqueous solutions so that the final concentrations of the additives became as shown in Table 21, thus preparing 30 kinds of aqueous solutions.

TABLE 21

| Additives | Concentration (%) |
|---|---|
| Gentiooligosaccharide[1] | 0.4 |
| Naringin | 0.0025 |
| Highly branched cyclic dextrin[2] | 0.07 |
| Magnesium chloride | 0.05 |
| Magnesium sulfate | 0.05 |

[1]gentiooligosaccharide syrup(Gentose#45: Produced by Nihon Shokuhin Kako Co., Ltd.,)
[2]Cluster Dextrin: Produced by Nihon Shokuhin Kako Co., Ltd.

Twelve panelists were asked to taste the resulting 30 kinds of aqueous solutions to evaluate the improvement in the sweetness quality of each sweetener attributable to each additive. The evaluation was conducted by scoring the improvement in sweetness quality based on the criteria described below in comparison with an aqueous solution containing only each of the sweeteners (Control).
Criteria
Improvement in sweetness quality: 2 points
Slight improvement in sweetness quality: 1 point
No Improvement in sweetness quality: 0 point
Table 22 shows the average scores by the twelve panelists.

TABLE 22

|  | Gentiooligo saccharide | Naringin | Highly branched cyclic dextrin | Magnesium chloride | Magnesium sulfate |
|---|---|---|---|---|---|
| Stevia extract | 1.7 | 1.3 | 1.8 | 1.7 | 1.8 |
| Siraitia grosvenorii extract | 1.0 | 0.7 | 0.7 | 1.5 | 0.5 |
| Licorice extract | 0.7 | 0.7 | 0.7 | 1.3 | 1.0 |
| Thaumatin | 0.8 | 0.7 | 0.5 | 1.0 | 1.3 |
| Aspartame | 0.3 | 0.3 | 0.3 | 0.8 | 0.7 |
| Neotame | 0.8 | 1.0 | 0.8 | 0.8 | 0.8 |

As shown in Table 22, all of the additives (gentiooligosaccharide, naringin, highly branched cyclic dextrin, magnesium chloride, and magnesium sulfate) reduced the remaining aftertaste of sweetness in stevia extract, and increased the richness (body) thereof. Among these, gentiooligosaccharide, magnesium chloride, magnesium sulfate, and highly branched cyclic dextrin exhibited remarkably excellent improvements in the sweetness quality of stevia extract.

However, these additives did not always improve the sweetness quality of other sweeteners (siraitia grosvenorii extract, licorice extract, thaumatin, aspartame, and neotame).

(III) Acceleration of Sweetness Expression in Stevia Extract

Example 15

Maltol was added to a 400-ppm aqueous solution of stevia extract in the proportions shown in Table 23 to prepare an aqueous solution containing stevia extract and maltol. A 400-ppm aqueous solution of stevia extract was prepared as a Control.

Eight panelists were asked to taste the resulting solutions to select the solutions that exhibited accelerated sweetness expression as compared to the Control. The results are shown in Table 23 together with the proportions of maltol.

TABLE 23

| Stevia extract (ppm) | 400 | 400 | 400 | 400 | 400 | 400 | 400 | 400 |
|---|---|---|---|---|---|---|---|---|
| Maltol (ppm) | 0.01 | 0.1 | 0.2 | 0.5 | 1 | 2 | 5 | 10 |
| Proportion (Stevia extract:Maltol) | 40000:1 | 40000:1 | 20000:1 | 800:1 | 400:1 | 200:1 | 80:1 | 40:1 |
| The number of panelists who answered that the expression of sweetness became faster and more favorable compared to the Control | 2 | 7 | 7 | 6 | 5 | 4 | 2 | 0 |

As shown in Table 23, more than half of the panelists answered that aqueous solutions containing at least 200 to 4,000 parts of stevia extract per part of maltol were more favorable in exhibiting quick sweetness expression in an oral cavity than an aqueous stevia extract solution (Control). An increased number of panelists answered that when the proportion of stevia extract was less than 200 parts per part of maltol, the smell of maltol became conspicuous and an unfavorable lingering sweetness (a remaining aftertaste) increased.

Example 16

Maltol was added to an aqueous solution of enzyme-treated stevia extract (SK Sweet FZ, produced by Nippon Paper Chemicals Co., Ltd., 600 ppm) in the proportions shown an Table 24 to prepare an aqueous solution containing enzyme-treated stevia extract and maltol. As a Control, a 600-ppm aqueous solution of enzyme-treated stevia extract was prepared. The 600-ppm aqueous solution of enzyme-treated stevia extract had almost the same degree of sweetness as the 400-ppm aqueous solution of stevia extract used in Example 15.

Eight panelists were asked to taste the stevia extracts to select the aqueous solutions that exhibited accelerated sweetness expression in an oral cavity compared to the Control (an aqueous solution of enzyme-treated stevia extract). Table 24 shows the results together with the proportions of maltol.

TABLE 24

| Enzyme-treated stevia extract (ppm) | 600 | 600 | 600 | 600 | 600 | 600 | 600 | 600 |
|---|---|---|---|---|---|---|---|---|
| Maltol (ppm) | 0.01 | 0.1 | 0.2 | 0.5 | 1 | 2 | 5 | 10 |
| Proportion (Stevia extract:Maltol) | 60000:1 | 60000:1 | 30000:1 | 1200:1 | 600:1 | 300:1 | 120:1 | 60:1 |
| The number of panelists who answered that the sweetness expression became faster | 3 | 4 | 6 | 8 | 7 | 4 | 3 | 1 |

As shown in Table 24, more than half of the panelists answered that aqueous solutions containing at least 300 to 6,000 parts of enzyme-treated stevia extract per part of maltol were favorable in exhibiting a faster sweetness expression in an oral cavity than an aqueous enzyme-treated stevia extract solution (Control). An increased number of panelists answered that when the proportion of enzyme-treated stevia extract was less than 300 parts per part of maltol, the smell of maltol became conspicuous and an unfavorable lingering sweetness (a remaining aftertaste) increased.

The results of Example 15 (Table 23) and Example 16 (Table 24) indicate that adding 200 to 6,000 parts, and preferably 300 to 6,000 parts, of stevia extract per part of maltol is effective for accelerating the sweetness expression of stevia extract.

Example 17

Carbonated Beverages Containing Lemon Juice (1) Preparation of Carbonated Beverages Lemon juice, citric acid (anhydrous) fine particles, trisodium citrate fine particles, stevia extract, 1% maltol and lemon flavoring were mixed in the proportion of the formula of Example 17 shown in Table 25. Water was added to the mixture so that the total amount of the water and mixed components became 20 parts, and the components were dissolved while stirring. Subsequently, carbonated water was added thereto to make the total amount 100 parts and the resulting mixture was placed in a container, obtaining a carbonated beverage containing lemon juice (Example 17). For comparison (Comparative Example), a carbonated beverage containing lemon juice was prepared in the same manner as Example 17 except that 1% maltol was not added.

TABLE 25

|  | Example 17 | Comparative Example |
|---|---|---|
| Lemon juice | 4.2 | 4.2 |
| Stevia extract | 0.033 | 0.033 |

TABLE 25-continued

|  | Example 17 | Comparative Example |
|---|---|---|
| 1% Maltol | 0.003 | — |
| Citric acid (anhydrous) fine particles* | 0.2 | 0.2 |
| Trisodium citrate fine particles* | 0.1 | 0.1 |
| Flavor (Lemon flavoring) | 0.1 | 0.1 |
| Total with water | 20.0 | 20.0 |
| Carbonated water | 80.0 | 80.0 |
| Total | 100.0 | 100.0 |

(2) Evaluation of Carbonated Beverages (Sensory Evaluation)

Ten panelists were asked to taste the resulting carbonated beverages (Example 17 and the Comparative Example) to evaluate the sweetness expression speed of the carbonated beverage of Example 17. The evaluation was conducted by comparing the sweetness expression speed of the carbonated beverage with that of the Comparative Example.

As a result of the sensory evaluation, the Comparative Example, which was prepared without adding maltol, exhibited a slow sweetness expression, and lingering sweetness was observed. In contrast, the carbonated beverage of Example 17, to which 0.3 ppm of maltol was added per 330 ppm of stevia extract, exhibited an accelerated sweetness expression, and the lingering sweetness was prevented. The carbonated beverage of Example 17 also achieved a sweetness quality similar to that of sucrose.

INDUSTRIAL APPLICABILITY

The present invention provides sweeteners, orally administered compositions and compositions used for the oral cavity (foods, beverages, medicines, and quasi drugs (including oral care products)) that contain a natural sweetener having an excellent sweetness quality.

The invention claimed is:

1. A high-intensity sweetener composition, consisting of a sweetener and carriers,
wherein the sweetener consists of rebaudioside A and mogroside V at a weight ratio of 95:5 to 60:40 (rebaudioside A:mogroside V), and wherein the carriers are at least one member selected from the group consisting of lactose, glucose, fructose, sucrose, high-fructose corn syrup, sugar alcohols, oligosaccharides, polysaccharides, and water.

* * * * *